United States Patent [19]

Grishin et al.

[11] 4,340,720
[45] Jul. 20, 1982

[54] PROCESS FOR PRODUCING HIGH-MOLECULAR POLYACETALS

[76] Inventors: Boris P. Grishin, ulitsa Bratskava, 8, kv. 75; Alexandr G. Gruznov, ulitsa Amurskaya, 31, kv. 72; Leonid M. Romanov, ulitsa Vavilova, 55/7, kv. 128; Julian I. Vishnyak, ulitsa Malenkovskaya, 7, kv. 1; Nina A. Shugaeva, ulitsa Oktyabrskaya, 6, korpus 1, kv. 2, all of Moscow; Nikolai M. Bychkov, Pavlovo-Posadsky R-N, 28, Sonino, Moskovskaya oblast; Konstantin V. Lipets, naberezhnaya Shevchenko, 1/2, kv. 55; Alexandr I. Zotov, Teply Stan, 1 mikroraion, korpus 7, kv. 240, both of Moscow, all of U.S.S.R.

[21] Appl. No.: 279,996

[22] PCT Filed: Nov. 30, 1979

[86] PCT No.: PCT/SU79/00125

§ 371 Date: Jul. 6, 1981

§ 102(e) Date: Jul. 30, 1981

[87] PCT Pub. No.: WO81/01556

PCT Pub. Date: Jun. 11, 1981

[51] Int. Cl.$^3$ ............................................. C08G 2/08
[52] U.S. Cl. .................................................. 528/232
[58] Field of Search ....................................... 528/232

[56] References Cited

U.S. PATENT DOCUMENTS 3,413,270  11/1968  Heinz et al. ........................ 528/232
3,657,189  4/1972  Ishida et al. ........................ 528/232
3,687,899  8/1972  Ackermann et al. ............... 528/232

FOREIGN PATENT DOCUMENTS 1336994  7/1963  France ............................... 528/232

*Primary Examiner*—Lucille M. Phynes
*Attorney, Agent, or Firm*—McAulay, Fields, Fisher, Goldstein & Nissen

[57] ABSTRACT

A process for producing high-molecular polyacetals, comprising polymerization of gaseous formaldehyde or copolymerization thereof with cyclic formals or cyclic oxides; formaldehyde is admitted into the reaction zone in a gas mixture which is the product of catalytic oxidative dehydrogenation of methanol, wherefrom $H_2O$, $CH_3OH$ and H COOH contaminants have been preliminarily removed. The process of polymerization or copolymerization is carried out in an inert hydrocarbon solvent in the presence of an ionic-type catalyst at a temperature within the range of from $-50°$ to $+120°$ C. with the formation of a vapor phase which is removed from the reaction zone.

1 Claim, No Drawings

PROCESS FOR PRODUCING HIGH-MOLECULAR POLYACETALS

FIELD OF THE INVENTION

The present invention relates to processes for producing high-molecular polyacetals.

BACKGROUND OF THE INVENTION

At present high-molecular polyacetals are produced in the form of homopolymers and copolymers. Homopolymer-structure polyacetals are formed by polymerization of formaldehyde or cyclic oligomers thereof. Copolymers are obtained by copolymerization of formaldehyde with various comonomers taken in an amount of from 2 to 3% by weight, i.e. the starting feedstock for the production of high-molecular polyacetals is monomeric formaldehyde or cyclic oligomers of formaldehyde such as trioxane or tetraoxane (cf. N. S. Enikolopyan, S. A. Volfson "Chemistry and Processing of Polyformaldehyde," "Khimiya" Publishers, Moscow, 1968, in Russian).

One of the ways for improving the process for the production of high-molecular polyacetals is to reduce the number of the process stages. More promising in this respect is the way, when as the starting feedstock for the production of high-molecular polyacetals, use is made of monomeric formaldehyde, since this enables the elimination of the stages of synthesis of intermediate products.

Commercial production of formaldehyde is based on catalytic oxidative dehydrogenation of methanol in the presence of air oxygen on metallic or oxide-type catalysts. The resulting formaldehyde is in the form of a mixture with different components: $H_2O$, $CH_3OH$, $HCOOH$, $N_2$, $CO_2$, $CO$, $H_2$, $CH_4$, $O_2$, and the like. The proportion of formaldehyde in the mixture depends on the catalysts employed and can vary from 2 to 19%. Recovery of formaldehyde from this mixture is effected, as a rule, by absorption thereof with water or alcohols. The resulting solutions can be used as a source for the production of concentrated monomeric formaldehyde or low-molecular polymers. Low-molecular polymers, in turn, can be used as a source for the production of monomeric formaldehyde through pyrolysis. To obtain concentrated monomeric formaldehyde, said solutions of formaldehyde are subjected to evaporation at a temperature within the range of from 110° to 130° C., followed by fractional condensation of vapours of water or an alcohol and separation thereof. Formaldehyde is thus produced in its monomeric form with the content of the main product ranging from 95 to 99%. The thus-recovered formaldehyde is subjected to further purification to the content of the main product of about 99.9%. For purification use is made of various physico-chemical methods based on profound condensation of impurities or chemical conversion thereof into different modifications, followed by separation.

Recovery and purification of monomeric concentrated formaldehyde constitute a multi-staged and complicated process due to an exclusively high chemical activity of formaldehyde and impossibility of storing it in its pure form (cf. J. Walker "Formaldehyde," Chemical Literature Publishing House, Moscow, 1957).

Therefore, difficulties associated with the recovery and purification of monomeric formaldehyde, impossibility of its storage in the pure form are serious obstacles in the way towards simplification of the process and reducing the production costs of the production of high-molecular polyacetals.

This is the basic factor hindering the extension of the manufacture of polyacetals on the basis of monomeric formaldehyde.

Known in the art are a number of processes for the production of high-molecular polyacetals by way of polymerization (copolymerization) of monomeric formaldehyde. Thus, known is a process comprising polymerization (copolymerization) of monomeric gaseous formaldehyde. To this end, the recovered and purified gaseous formaldehyde is fed into a reactor containing an inert hydrocarbon solvent and an ionic-type catalyst. In the case of copolymerization a comonomer such as cyclic formals, cyclic oxides is additionally introduced into the reactor. The polymerization (copolymerization) is carried out at a temperature within the range of from −50° to +120° C. The evolving reaction heat in the amount of 15.0-16.0 kcal/mol $CH_2O$ is removed through the reactor walls by means of a suitable coolant (J. Furukawa and T. Saegusha "Polymerization of Aldehydes and Oxides," "Mir" Publishers, Moscow, 1965).

As it has been mentioned hereinabove, a great quantity of heat is evolved during polymerization (copolymerization) of gaseous formaldehyde.

It should be noted that the reaction heat can be removed by heat-transfer process only in the case of small-size reactors. In large-size reactors the ratio of the heat-transfer surface to the reactor volume is decreased, thus causing intentional decreasing of the polymerization (copolymerization) rate by lowering the unit load of formaldehyde in g $CH_2O$ per liter of the liquid phase per unit of time.

It has been found that, all other factors being equal, molecular weight of the polymer decreases with a reduced unit load of formaldehyde. Thus, the polymer viscosity determined in a 0.5% solution of dimethylformamide at the temperature of 150° C. diminishes from 0.68 to 0.57 dl/g respectively with the unit load being lowered from 15 to 2 g/l per minute.

The technique of the heat removal through the reactor walls does not make it possible to carry out a continuous process of polymerization (copolymerization) of gaseous formaldehyde due to deposition of the polymer film on the reactor walls, which substantially impairs the heat transfer process. The reactor should be periodically cleaned to remove the polymer film from the wall surface.

Technologically more efficient is the removal of the reaction heat by way of evaporation of the liquid phase and removal of its vapours from the reaction zone by means of an inert gas specifically introduced for this purpose.

Known in the art is a process for producing high-molecular polyacetals by polymerization of monomeric gaseous formaldehyde in an inert liquid containing an ionic catalyst (cf. Japanese Patent No. 8223 Cl. C 08 g 26, published on March 3, 1972). The process comprises supplying gaseous formaldehyde containing 99.8% of the main product into a reactor filled with n-hexane incorporating a catalyst—1.38% by weight of di-n-butyltindialurate at the temperature equal to 50° C. At the same time, through a special pipe, separately from admission of formaldehyde, an inert gas, i.e. nitrogen, is fed. The resulting vapours of n-hexane are withdrawn from the reactor together with the inert gas. In this manner the reaction heat is removed and the required temperature conditions are maintained.

The above-discussed process makes it possible to solve the problem of removing the reaction heat; however, as the starting stock in this process use is made of concentrated formaldehyde and, hence, this process involves all the above-discussed difficulties, associated with the recovery and purification of gaseous formaldehyde.

In this respect, of certain interest is the process for producing high-molecular polyacetals, wherein as the starting feedstock use is made of a solution of formaldehyde in an inert hydrocarbon, formaldehyde being obtained from the reaction gases of catalytic oxidative dehydrogenation of methanol (cf. French Pat. No. 1,336,994). According to this Patent, the reaction gases from oxidation of methanol are purified from $H_2O$, $CH_3OH$ and $HCOOH$ contaminants by fractional condensation and removal of these impurities. Thereafter, to carry out profound purification to the content of the contaminants down to 0.1% by weight, the remaining gaseous mixture is passed through a vessel containing n-heptane incorporating 0.01% of n-butylamine at the temperature of $-10°$ C.

The reaction mixture decontaminated from $H_2O$, $CH_3OH$ and $HCOOH$ is then fed into an absorber to recover pure formaldehyde by absorption thereof with an inert hydrocarbon (toluene) at the temperature of $-70°$ C. The thus-obtained solution of formaldehyde in toluene is free from admixtures of other components otherwise present in the starting reaction gases available from oxidation of methanol, namely: $N_2$, $CO_2$, $CO$, $CH_4$, $H_2$, $O_2$, and the like, and constitutes the starting feedstock for the production of high-molecular polyacetals. This solution of pure formaldehyde is admitted into the reactor, whereinto added is a polymerization catalyst, i.e. n-butylamine. Polymerization of formaldehyde takes place in the reactor.

This process is distinguished from the prior art processes described hereinbefore by that the solution of formaldehyde in an inert liquid as used at the polymerization stage is obtained directly from the reaction gases of the oxidative dehydrogenation of methanol after decontaminating them from $H_2O$, $CH_3OH$ and $HCOOH$. However, the necessity in obtaining the solution of formaldehyde in an inert liquid substantially complicates the process and lowers its economical efficiency.

DISCLOSURE OF THE INVENTION

The present invention is directed to the provision, in the process for producing high-molecular polyacetals, of such starting feedstock which would make it possible to simplify the process flow sheet and improve economic factors of the production.

This object is accomplished by that in the process for the production of high-molecular polyacetals by polymerization of gaseous formaldehyde or copolymerization thereof with cyclic formals or cyclic oxides in an inert hydrocarbon solvent in the presence of an ionic catalyst at a temperature within the range of from $-50°$ to $+120°$ C. with the formation of the vapour phase which is withdrawn from the reaction zone, in accordance with the present invention, formaldehyde is fed into the reaction zone in a gas mixture which is the product of catalytic oxidative dehydrogenation of methanol, from which mixture $H_2O$, $CH_3OH$ and $HCOOH$ are removed prior to the admission thereof into the reaction zone.

As cyclic formals use can be made of, for example, derivatives of glycols and formaldehyde, in particular 1,3-dioxolane, 1,3,5-trioxepane, 1,4-butanediol formal.

As the inert hydrocarbon solvent use can be made, for example, of aliphatic, cycloaliphatic and aromatic hydrocarbons, their halides and esters.

The above-specified solvents are a liquid phase present in the formaldehyde polymerization zone. In the case of copolymerization of formaldehyde the liquid phase also incorporates a comonomer.

As the catalysts in the process according to the present invention use is made of ionic-type catalysts. In particular, it is possible to use oxides, hydroxides and salts of alkali and alkali-earth metals, amines, Lewis acids, complexes of Lewis acids with bases.

The selected range of polymerization (copolymerization) temperatures is wide enough to enable the use of ionic-type catalysts. Within this range it is not difficult to effect the polymerization (copolymerization) heat removal by evaporation of the liquid phase and withdrawal of its vapours with the vapour phase. The polymerization (copolymerization) temperature depends on the nature of the liquid phase, on the content of formaldehyde in the starting gas mixture and on the polymerization (copolymerization) pressure.

As the reaction gases from the catalytic oxidative dehydrogenation of methanol, use can be made of the reaction gases obtained from oxidation of methanol on metallic of oxide catalysts containing $H_2O$, $CH_3OH$, $HCOOH$, $N_2$, $CO_2$, $CO$, $H_2$, $CH_4$, $O_2$, and the like. It has been found that among these components only $H_2O$, $CH_3OH$ and $HCOOH$ are detrimental for the polymerization (copolymerization) of formaldehyde, since being chain-propagation agents during the process of polymerization (copolymerization), they reduce the molecular weight of the product.

After the removal of these contaminants, the gas mixture is a mixture of formaldehyde with gases inert to polymerization (copolymerization), the concentration of formaldehyde in this mixture varying from 5 to 50% by volume.

The use, as the starting feedstock, of the gas mixture which is the product of catalytic oxidative dehydrogenation of methanol freed from certain contaminants makes it possible to essentially lower the expenditures for the production of high-molecular polyacetals, since the feedstock employed is considerably less expensive than the feedstock employed hitherto—concentrated gaseous formaldehyde or solutions of formaldehyde in inert hydrocarbons.

The use, as the starting feedstock, of the reaction gas mixtures from the catalytic oxidative dehydrogenation of methanol also makes it possible to substantially simplify the process equipment, for example, at the stage of feedstock transportation into the reaction zone, and to solve the problem of removal of the polymerization (copolymerization) heat due to the evaporation of the liquid phase and entrainment of its vapours from the reaction zone without special admission of inert gases for this purpose.

The process according to the present invention can be effected continuously at a high polymerization rate over 5 g/l per minute, i.e. with high unit loads, whereby the process is substantially intensified and a high-quality product is obtained.

The process for producing high-molecular polyacetals according to the present invention is simple and can be effected in the following manner.

The reaction gases obtained from catalytic oxidative dehydrogenation of methanol are subjected to decontamination from $H_2O$, $CH_3OH$ and $HCOOH$ by conventional methods. For this purpose use can be made of, for example, the method based on passing gases at the temperature of $-15°$ C. through a liquid containing a catalyst, or the method comprising contacting the reactive gases from the catalytic oxidative dehydrogenation of methanol with an inert substance cooled to a temperature of $-20°$ to $-75°$ C. As a result of such purification the starting gas mixture is fully freed from contaminating $H_2O$, $CH_3OH$ and $HCOOH$; the resulting mixture contains formaldehyde in an amount of from 5 to 50% by volume (depending on the catalyst employed at the stage of oxidative dehydrogenation of methanol and conditions of purification from the above-specified contaminants), as well as all the remaining components: $CO_2$, $N_2$, $CH_4$, $H_2$, $O_2$, and the like.

The resulting has mixture is fed into a reactor, whereinto an inert solvent and an ionic-type catalyst have been preliminarily placed. The catalyst is employed in an amount of from $10^{-2}$ to $10^{-4}$ mol/l. In the case of copolymerization a comonomer is also charged into the reactor in an amount ranging from 0.5 to 50% by weight of the solvent. The polymerization (copolymerization) of formaldehyde is carried out at a temperature of from $-50°$ to $+120°$ C. During the reaction heat is continuously liberated in an amount of 15-16.0 kcal/mol of $CH_2O$. This heat is consumed for evaporation of the liquid phase. The resulting vapours are mixed with gases, thus making up a vapour phase, and then they are withdrawn from the reaction zone.

The high-molecular polyacetal formed in the polymerization (copolymerization) is present in the liquid phase as a disperse solid phase (suspension) which is recovered by conventional techniques (centrifugation, filtration and the like).

When the process is carried out continuously, the resulting suspension is continuously withdrawn from the reactor, while continuously added thereinto are the starting gas mixture and the starting components including the catalyst in amounts equal to the amount of these components, withdrawn from the reaction zone as the vapour phase and the resulting suspension of the product.

The rate of admission of the gas mixture is selected so as to ensure the unit load of formaldehyde relative to the liquid phase equal to at least 5.0 g of $CH_2O$ l/min.

The obtained product is thermostabilized: the homopolymer—by acetylation of the terminal groups with acetic anhydride; the copolymer—by heat-treatment in a 7% aqueous solution of $NH_3$ at the temperature of 140° C.

The molecular weight of the product is evaluated by determining its viscosity in 0.5% solution in dimethylformamide at the temperature of 150° C.

For a better understanding of the present invention some specific examples are given hereinbelow by way of illustration.

EXAMPLE 1

A metallic reactor, 100 mm in diameter and 600 mm in height, provided with a thermometer and a stirrer is filled, to ½ of its height, with ethylbenzene containing 3% by weight of 1.3-dioxolane. Also charged into the reactor is a catalyst $(C_4H_9)_2OBF_3$ in the amount of $3.10^{-3}$ mol/l.

A gas mixture obtained from oxidative dehydrogenation of methanol is charged into the reactor; it has been preliminarily freed from contaminating $H_2O$, $CH_3OH$ and $HCOOH$ by contacting the gas mixture with a cooled (to $-40°$ C.) inert hydrocarbon. The total amount of the above-mentioned contaminants in the gas mixture after purification is not more than 0.005% by weight. The content of formaldehyde in this gas mixture after purification is 22% by volume. The temperature of the copolymerization process is 41°-43° C. The copolymerization of formaldehyde with 1,3-dioxolane is effected in the presence of gaseous $CO_2$, $CO$, $N_2$, $CH_4$, $H_2$, $O_2$, and the like. The reaction heat is consumed for the formation of vapours of the liquid phase, which are continuously withdrawn from the reactor with the off-gases. The vapours entrained by the off-gases are condensed in a special condenser placed outside the reaction zone and are again recycled into the reactor.

The resulting desired product is a solid phase dispersed in the liquid phase. As the product accumulates in the amount of 40% by weight of the liquid phase, continuous withdrawal of the suspension from the reactor is started, while the starting mixture: ethylbenzene, 1,3-dioxolane and the catalyst is added into the reactor so that the amounts of the components introduced are equal to the amounts thereof withdrawn from the reactor. In this manner the continuous process of copolymerization of formaldehyde with 1.3-dioxolane is effected.

The thus-prepared product has the viscosity determined for a 0.5% solution of the copolymer in dimethylformamide at the temperature of 150° C. equal to: $\eta=0.54$ at the rate of the gas mixture supply of 10 l/min and $\eta=0.66$ at the rate of the gas mixture supply of 70 l/min.

EXAMPLE 2

The metallic reactor described in the foregoing Example 1 is filled to ½ of its height with gasoline containing 2% by weight of 1,3,5-trioxepane. Also charged into the reactor is the catalyst $(But)_2O.BF_3$ in the amount of $5.10^{-3}$ mol/l. Gasoline comprises a mixture of aromatic, aliphatic and naphthol hydrocarbons, boiling within the range of from 117° to 143° C.

Continuously fed into the reactor is the gas mixture obtained from oxidative dehydrogenation of methanol, wherefrom impurities of $H_2O$, $CH_3OH$ and $HCOOH$ are removed prior to the admission into the reactor by contacting the gas mixture with a cooled inert hydrocarbon. The content of formaldehyde in the gas mixture after purification is 19% by volume. The temperature of the copolymerization product is equal to 57°-65° C. This temperature is maintained due to evaporation of the liquid phase and entrainment of its vapours from the reaction mixture by the off-gases. The vapours removed together with the off-gases are condensed in a condenser placed outside the reaction zone and recycled into the reactor. As the product is accumulated in the amount of 40% by weight of the liquid phase, continuous withdrawal of the suspension from the reactor is started; the starting mixture containing gasoline, 1,3,5-troxepane and the catalyst is continuously fed into the reactor in amounts equal to those withdrawn from the reactor.

The viscosity of the 0.5% solution of the obtained copolymer in dimethylformamide as measured at the temperature of 150° C. is $\eta = 0.58$–$0.61$ dl/g.

EXAMPLE 3

A glass vessel with the diameter of 35 mm, height of 300 mm, provided with a thermometer and having an enlarged upper section is filled with toluene to $\frac{2}{3}$ of its volume. Into the vessel there is also charged a catalyst—calcium stearate in the amount of $6.10^{-3}$ mol/l. Through a bubbling tube lowered to the vessel bottom a gas mixture is passed, obtained from the oxidative dehydrogenation of methanol and preliminarily purified from $H_2O$, $CH_3OH$ and $HCOOH$. The content of formaldehyde in the gas mixture is 21% by volume. The rate of admission of the gas mixture is 5 l/min. The polymerization time is 21 minutes. The temperature of polymerization of formaldehyde is 20° C. There are obtained 19.7 g of a homopolymer having viscosity of its 0.5% solution in dimethylformamide at the temperature of 150° C. equal to $\eta = 0.71$ dl/g.

EXAMPLE 4

The glass vessel described in the foregoing Example 3 is filled to $\frac{2}{3}$ of its volume with ethylbenzene containing 25% by weight of 1,3-dioxolane. Into the vessel a catalyst, i.e. $(But)_2OBF_3$ is charged and the vessel is thermostatted at the temperature of 40° C. Through the bubbling tube extending to the vessel bottom a gas mixture is passed which has been obtained from the oxidative dehydrogenation of methanol and freed from $H_2O$, $CH_3OH$ and $HCOOH$. The content of formaldehyde in the gas mixture is 48% by volume. The rate of admission of the gas mixture is 3 l/min. The time of copolymerization is 1.5 hours. The conversion of formaldehyde to the copolymer is equal to 96%.

The viscosity of 0.5% solution of the resulting copolymer in dimethylformamide as measured at the temperature of 150° C. is 0.66 dl/g.

EXAMPLE 5

The glass vessel described in Example 3 hereinbefore is filled with n-butane to $\frac{2}{3}$ of its volume. The reactor contents are brought to the temperature of $-22°$ C., added with 2% of ethylene oxide by weight of n-butane and a catalyst, i.e. $(But)_2OBF_3$ in the amount of $7.10^{-3}$ mol/l. Through the bubbling tube extending to the bottom of the vessel a gas mixture is passed which has been obtained from the oxidative dehydrogenation of methanol and preliminarily freed from $H_2O$, $CH_3OH$ and $HCOOH$. The content of formaldehyde in the gas mixture is 21% by volume. The rate of admission of the gas mixture is 6 l/min. The conversion of formaldehyde to the copolymer is 79%.

The viscosity of 0.5% solution of the copolymer in dimethylformamide as determined at the temperature of 150° C. is equal to $\eta = 0.43$ dl/g.

EXAMPLE 6

A metallic reactor comprising a cylindrical vessel with the diameter of 37 mm and height of 300 mm is filled to $\frac{2}{3}$ of its volume with toluene containing a catalyst, i.e. calcium stearate in the amount of $8.10^{-3}$ mol/l. The reactor is thermostatted at the temperature of 75° C. and the gas mixture is admitted thereinto under the pressure of 2.0 atm.g. The mixture is obtained from oxidative dehydrogenation of methanol and preliminarily freed from $H_2O$, $CH_3OH$ and $HCOOH$ contaminants. The content of formaldehyde in the gas mixture is 9% by volume. The rate of admission of the gas mixture is equal to 5 l/min. During polymerization the temperature is elevated to 92°–95° C. The polymerization time is 25 minutes. The resulting homopolymer has the viscosity of its 0.5% solution in dimethylformamide at the temperature of 150° C. equal to $\eta = 0.47$ dl/g.

Properties of the resulting products are shown in the table hereinbelow.

| Properties | Characteristics | |
|---|---|---|
| | Homopolymer | Copolymer |
| Melt index at 190° C. g/10 min | 2.5–10 | 5.5–15.0 |
| Tensile strength at 20° C., kgf/cm$^2$ | 700–710 | 650–700 |
| Density at 20° C., g/cm$^3$ | 1.42 | 1.41 |
| Relative elongation at rupture, % | 15–45 | 25–40 |
| Specific impact viscosity of notched samples at 20° C., kgf . cm/cm$^2$ | 7.5–12.5 | 6.0–8.0 |

Industrial Applicability

High-molecular polyacetals produced by the process according to the present invention find extensive use in the industry. Polyacetals are thermoplastic materials possessing a range of valuable mechanical properties which render them competitive with non-ferrous metals in the manufacture of various structural parts, e.g. in instrument making and mechanical engineering, electrical engineering.

Best Mode for Carrying Out the Invention

The reaction gases from the catalytic oxidative dehydrogenation of methanol are subjected to purification from $H_2O$, $CH_3OH$ and $HCOOH$ contaminants by contacting them with a cooled inert liquid at the temperature of $-40°$ C. The resulting gas mixture substantially free from the above-specified impurities is fed into a reactor preliminarily charged with an inert hydrocarbon solvent and an ionic-type catalyst.

The rate of supply of the gas mixture is selected so as to ensure a unit load of formaldehyde relative to gasoline 15.0 g/l per minute. The selected copolymerization temperature is maintained due to the formation of vapours of the liquid phase and the removal thereof in a mixture with the off-gases. In the condenser positioned outside the reaction zone the vapour phase is condensed and continuously recycled into the reactor. When the solid phase of the disperse polymer (copolymer) is accumulated in the amount of 60% by weight of the liquid phase present in the reactor, the resulting suspension is started to be withdrawn from the reactor.

The amount of the liquid phase in the reactor is continuously replenished by continuously adding the starting components (inert hydrocarbon and catalyst; comonomer—in the case of copolymerization) in the amounts equal to those withdrawn from the reactor.

The solid phase of the polymer (copolymer) withdrawn as a suspension is separated from the liquid phase; the latter in the amount of 90% by weight is recycled into the reactor.

The thus-produced polymer (copolymer) is subjected to thermostabilization and its quality is then determined.

The viscosity of 0.5% solution of the product in dimethylformamide at the temperature of 150° C. is equal to $\eta = 0.64$ dl/g.

We claim:

1. A process for producing high-molecular polyacetals by polymerization of gaseous formaldehyde or copolymerization thereof with cyclic formals or cyclic oxides in an inert hydrocarbon solvent in the presence of an ionic-type catalyst at a temperature within the range of from $-50°$ to $+120°$ C. with the formation of a vapour phase, characterized in that formaldehyde is admitted into the reaction zone in a gas mixture which is the product of a catalytic oxidative dehydrogenation of methanol, wherefrom $H_2O$, $CH_3OH$ and $HCOOH$ have been preliminarily removed.

* * * * *